(12) United States Patent
Mueller et al.

(10) Patent No.: US 7,997,435 B2
(45) Date of Patent: Aug. 16, 2011

(54) CONTAINER FOR A PLURALITY OF TEST STRIPS

(75) Inventors: Peter Mueller, Griesheim (DE); Horst Langkau, Darmstadt (DE); Berthold Wagner, Frankfurt am Main (DE); Gerhard Wieland, Bensheim (DE); Norbert Stork, Darmstadt (DE); Stefan Bernhard, Erbach (DE)

(73) Assignee: Merck Patent GmbH, Darmstadt (DE)

( * ) Notice: Subject to any disclaimer, the term of this patent is extended or adjusted under 35 U.S.C. 154(b) by 4 days.

(21) Appl. No.: 12/593,445

(22) PCT Filed: Feb. 29, 2008

(86) PCT No.: PCT/EP2008/001607
§ 371 (c)(1),
(2), (4) Date: Sep. 28, 2009

(87) PCT Pub. No.: WO2008/119421
PCT Pub. Date: Oct. 9, 2008

(65) Prior Publication Data
US 2010/0108546 A1 May 6, 2010

(30) Foreign Application Priority Data

Mar. 29, 2007 (DE) .......................... 10 2007 015 100

(51) Int. Cl.
*B65D 41/32* (2006.01)
(52) U.S. Cl. ........ 220/266; 220/265; 220/787; 220/784; 206/456; 206/268
(58) Field of Classification Search .................. 220/788, 220/787, 784, 265, 266; 215/253; 206/268, 206/449, 456, 1.5, 540
See application file for complete search history.

(56) References Cited

U.S. PATENT DOCUMENTS
2,960,264 A * 11/1960 Walter .......................... 206/266
(Continued)

FOREIGN PATENT DOCUMENTS
DE 32 44 459 A1 6/1983
(Continued)

OTHER PUBLICATIONS
International Search Report of PCT/EP2008/001607 (Jul. 23, 2008).

*Primary Examiner* — David T Fidei
(74) *Attorney, Agent, or Firm* — Millen, White, Zelano & Branigan, P.C.

(57) ABSTRACT

A container (1) for a plurality of test strips, in particular for strip-shaped indicator sticks, has a housing lower part (2) and a housing upper part (3), which can be brought into engagement with the housing lower part (2) in a positive manner, where the housing upper part (3) has an opening with a sealing flap (14) mounted in a pivotable manner, where the housing lower part (2) has a plurality of projecting snap-in elements (7), which can be brought into engagement with matched recesses (10) of the housing upper part (3), and where the sealing flap (14) is connected along its periphery to the housing upper part (3) by means of at least one connecting strip which can be torn off. The snap-in elements (7) project by more than one wall thickness of the housing upper part (3) in the region around the recesses (10). The sealing flap (14) preferably has a tear-off connecting strip on each of two opposite sides. The sealing flap (14) is preferably mounted in a pivotable manner on the housing lid (15) of the housing upper part (3) and forms a corner (13) of the housing upper part (3). The length of the sealing flap (14) along the housing lid (15) is preferably less than the length of the sealing flap (14) along the side wall (24) of the housing upper part (3).

6 Claims, 5 Drawing Sheets

U.S. PATENT DOCUMENTS

| | | | |
|---|---|---|---|
| 3,872,996 A * | 3/1975 | Dogliotti | 220/254.7 |
| 4,434,907 A | 3/1984 | Ingemann | |
| 4,463,869 A | 8/1984 | Lewis | |
| 4,538,731 A * | 9/1985 | Cillario | 206/540 |
| 4,615,462 A | 10/1986 | Sacherer et al. | |
| 4,717,018 A | 1/1988 | Sacherer et al. | |
| 4,724,977 A | 2/1988 | Cleevely et al. | |
| 4,934,556 A | 6/1990 | Kleissendorf | |
| 5,176,275 A * | 1/1993 | Bowie | 220/201 |
| 5,505,308 A | 4/1996 | Eikmeier et al. | |
| 6,095,364 A * | 8/2000 | Dickie et al. | 220/259.5 |
| 6,112,889 A * | 9/2000 | Wicker | 206/213.1 |
| 6,929,120 B2 * | 8/2005 | Zonker et al. | 206/268 |
| D548,585 S * | 8/2007 | Okabe et al. | D9/420 |
| 7,611,027 B2 * | 11/2009 | Kim | 215/305 |
| 7,654,411 B2 * | 2/2010 | Boots et al. | 220/835 |
| 2003/0197013 A1 * | 10/2003 | Conti et al. | 220/297 |
| 2005/0281706 A1 | 12/2005 | Funke et al. | |
| 2006/0118570 A1 | 6/2006 | Fowler et al. | |

FOREIGN PATENT DOCUMENTS

| | | |
|---|---|---|
| DE | 88 00 462 U1 | 2/1988 |
| DE | 196 53 065 A1 | 6/1998 |
| DE | 199 09 426 A1 | 5/2000 |
| EP | 0 167 783 A1 | 1/1986 |
| EP | 0 270 868 A1 | 6/1988 |
| EP | 0 618 146 A2 | 10/1994 |
| EP | 0 640 393 A1 | 3/1995 |
| EP | 1 167 221 A1 | 1/2002 |
| WO | WO 2006/009534 A1 | 1/2006 |

* cited by examiner

CONTAINER FOR A PLURALITY OF TEST STRIPS

The invention relates to a container for a plurality of test strips, in particular for strip-shaped indicator sticks, having a housing lower part and a housing upper part, which can be brought into engagement with the housing lower part in a positive manner, where the housing upper part has an opening with a sealing flap mounted in a pivotable manner.

Containers for strip-shaped indicator sticks have been known for some time in practice. These containers usually consist of a cuboid housing lower part open on one side and a likewise cuboid housing upper part open on one side, where the housing upper part can be pushed onto the housing lower part to form a container which is closed on all sides. The housing upper part is held on the housing lower part in a non-positive manner.

The dimensions of the housing lower part and housing upper part are matched to the dimensions of the strip-shaped indicator sticks. The lid and the mutually opposite side faces of the housing upper part and the base and the opposite side faces of the housing lower part are matched to the width of the strip-shaped indicator sticks. The container usually has a housing lower part which, in length, covers more than half of the indicator sticks stored therein, and a significantly smaller housing upper part.

Containers of this type can be produced rapidly and inexpensively. They can be filled and sealed automatically in a simple manner.

However, containers of this type do not have protection of originality. It cannot be ascertained whether the container has already been opened and resealed. If the contents of the container make protection of originality necessary, either the container must, for example, be introduced completely into a film wrapping which can be torn open, or alternatively each individual test strip must be provided with protection of originality, for example with a tear-open wrapping which must be removed on first use and cannot be put on again. Protection of originality of this type is material-intensive and requires separate application of a wrapping, which is associated with additional costs.

The handling of containers of this type is also often regarded as impractical, since, in order to remove an indicator stick, the housing upper part must be removed completely and then all indicator sticks may fall out of the housing lower part, which is open on one side.

Various designs of containers are known (for example US 2005/0281706 A1, EP 0 270 868 B1, EP 0 640 393 B1, WO 2006/009534 A1, US 2006/0118570 A1), which are intended to facilitate the removal of a single test strip in a simple manner. However, the design complexity necessary for this purpose is very high. Removal devices of this type can easily be damaged, at least partly, and not uncommonly have malfunctions, meaning that a test strip can no longer be removed or the test strip is removed from the container in a damaged state. The known containers which can be used as test strip dispensers additionally often do not have protection of originality.

Other containers are known (for example EP 1 167 221 A1, U.S. Pat. Nos. 4,934,556, 4,463,896, DE 32 44 459 C2, EP 0 618 146 A2, DE 196 53 065 A1, EP 0 167 783 A1) which generally have a sealing cap which is connected to the container via a separate tear-off element. The sealing cap can only be opened and resealed after the tear-off element has been removed. The tear-off element here generally has to be detached completely from the sealing cap and the container and disposed of, which may be associated with not inconsiderable effort, in particular on use in chemical/pharmaceutical laboratories or at workplaces which make increased requirements of cleanliness and disposal. The production complexity is also high for containers of this type. The containers are not suitable or are only of limited suitability for the accommodation of test strips. Simple and reliable removal of the test strips is only rarely possible.

In a container of the generic type mentioned at the outset (U.S. Pat. No. 4,724,977), the housing upper part can be connected to the housing lower part in a positive manner and has a flat, resealable closure in the region of the lid of the housing upper part and a removable closure arranged immediately thereunder. When the container is opened for the first time, the resealable closure arranged in a pivotable manner must firstly be opened and the removable closure located thereunder must then be separated out and removed. The removable closure cannot be re-inserted into the housing upper part. After use, the container can be resealed by the resealable closure.

In order to prevent undesired opening of the container by detachment of the housing upper part from the housing lower part, it is provided that the housing upper part engages over a bead-like thickening of the housing lower part and is made of a sufficiently dimensionally stable material that the housing upper part cannot be pulled off the housing lower part and can be re-connected thereto without this resulting in damage to the container. The effort for the production of the complex-shaped housing upper part and for the attachment of the housing upper part to the housing lower part is considerable. Simple handling of this container during removal of test strips is made more difficult by the inward-projecting shapes along the periphery of the closure in the housing upper part, which remain in the housing upper part after removal of the removable closure and behind which individual test strips may become caught.

The object of the present invention is accordingly to design a container for a plurality of test strips in such a way that the container is provided with simple means with protection of originality and at the same time facilitates simple handling or removal of a test strip.

This object is achieved in accordance with the invention in that a plurality of projecting snap-in elements which can be brought into engagement with matched recesses of the housing upper part, are arranged on the housing lower part, and that the sealing flap is connected along its periphery to the housing upper part by means of at least one connecting strip which can be torn off.

The projecting snap-in elements on the housing lower part are brought into engagement with the matched recesses in the housing upper part when the housing upper part is pushed onto the housing lower part and form a snap-in connection which can no longer be disconnected non-destructively. The sealing flap is connected to the housing upper part via at least one tear-off connecting strip in such a way that the at least one connecting strip is torn off when the sealing flap is first opened and thus reliably indicates that the sealing flap has already been opened. The fact that the housing upper part is connected to the housing lower part in such a manner that it cannot be disconnected non-destructively and the tear-off connecting strips indicate first opening of the sealing flap arranged in the housing upper part enables reliable protection of originality with means of simple design.

The projecting snap-in elements and the matched recesses as well as the at least one tear-off connecting strip can be produced simply and inexpensively without additional material or increased complexity being necessary during production. Automated filling is not made more difficult since the housing upper part can be connected to the housing lower part without noticeably greater exertion of force if the projecting snap-in elements are suitably designed. The outer dimensions of the housing upper part and housing lower part do not necessarily have to differ noticeably from the dimensions of the containers already known from practice for strip-shaped indicator sticks, so that major expense does not arise on conversion from the containers without protection of originality that are already known from practice to the containers with protection of originality that are described above.

It is preferably provided that the snap-in elements project by more than half the wall thickness of the housing upper part in the region around the recesses, preferably by more than three quarters of the wall thickness and particularly preferably by more than one wall thickness of the housing upper part. Depending on the material used for the housing upper part, the snap-in elements must in any case project sufficiently far in order to destroy the housing upper part on detachment from the housing lower part or at least to leave behind visible traces that lastingly indicate forcible detachment.

It is advantageous here for the snap-in elements to have, on the side facing the housing upper part, an inclined sliding surface which simplifies pushing-on of the housing upper part and to have, on the side facing the housing lower part, a stop face which projects perpendicular to the surface.

The snap-in elements are advantageously arranged in the region of side edges of the housing lower part. In this way, a side face of the housing upper part with the recesses arranged therein is prevented from being lifted by the housing lower part, for example with the assistance of a flat aid, in order to disengage the snap-in elements from the recesses and to separate the housing upper part from the housing lower part non-destructively.

In order further to hinder non-destructive detachment of the housing upper part from the housing lower part, it is provided that the wall thickness of the housing lower part is reduced by at least the wall thickness of the housing upper part in the region of the overlap by the housing upper part. If the narrowing of the housing lower part is matched to the wall thickness of the housing upper part, the housing upper part can be pushed onto the housing lower part in such a way that the outside surfaces of the housing upper part are subsequently aligned and arranged flush and jointlessly with the corresponding outside surfaces of the housing lower part. Gaps or joins and projecting shapes, which could simplify or facilitate mechanically forced separation and detachment of the housing upper part from the housing lower part, are thus avoided.

It is likewise conceivable for both the wall thickness of the housing lower part and also the wall thickness of the housing upper part to be essentially comparable and for each to be reduced matched to one another in the region of the overlap. The housing upper part can then be pushed onto the housing lower part in such a way that both the outside surfaces and also the inside surfaces of the housing upper part and of the housing lower part abut one another in an essentially flush and jointless manner. The wall thickness of the container is then constant. Undesired steps and projecting edges are avoided both on the inside surfaces and also on the outside surfaces.

In order to enable simple and inexpensive production and at the same time to ensure reliable protection of originality of the sealing flap, it is advantageously provided that the sealing flap has at least one tear-off connecting strip on each of two opposite sides. The sealing flap advantageously has an essentially rectangular periphery or edge, which also limits the opening in the housing upper part. The sealing flap is mounted in a pivotable manner on the housing upper part, for example by means of a film hinge along one side of the sealing flap. A tear-off connecting strip, which connects the sealing flap to the housing upper part and only releases the sealing flap and allows it to be opened when it has been torn off, is formed on each of the opposite sides adjacent to the film hinge on both sides.

A clamping or positive closure device, which fixes or retains the sealing flap in a detachable manner to the housing upper part in a closed position, may be provided on the side of the sealing flap which is opposite the film hinge. This can be achieved in a simple manner by a snap-in tongue moulded on the sealing flap engaging behind the elastically deformable edge of the opening of the housing upper part when the sealing flap is closed and retaining the sealing flap in the closed position. It is also conceivable to design the snap-in tongue of the sealing flap to be elastically deformable instead of the edge of the opening of the housing upper part, or additionally thereto, or to form a snap-in tongue at the edge of the opening of the housing upper part.

The shape of the tear-off connecting strips can be specified virtually as desired and matched to the respective requirements during production of the housing upper part, the material used and the protection of originality desired. It has proven particularly advantageous for the tear-off connecting strips to be formed as narrow and, relative to the wall thickness, tapered transitions of a separation join otherwise forming around the edge of the sealing flap. It is of course also possible for a plurality of tear-off connecting strips to be provided, which connect the sealing flap to the housing lower part, either at a uniform or irregular separation.

According to a particularly advantageous embodiment of the inventive idea, it is provided that the opening which can be sealed by the sealing flap encompasses both a region of a housing lid and also a region of a side wall of the housing upper part. It has been found that the removal of a single test strip is considerably simplified if the opening is not arranged exclusively in the region of the housing lid and thus on the upper side of the container. The fact that the opened sealing flap also uncovers part of the side wall of the housing upper part means that, for removal of a test strip, the container can be held in a slightly tilted manner so that an end region of a test strip is freely accessible both from the top and also from the side, and the test strip can be easily grasped and removed. Complete rotation or inversion of the container, as necessitated by openings arranged solely in the region of the housing lid, is unnecessary. The risk known from practice of a number of test strips, or even all of them, falling out of the container during removal of a single test strip can thus be reduced or completely suppressed.

In order to simplify simple removal of a test strip, it is provided that the sealing flap is mounted in a pivotable manner on the housing lid of the housing upper part and forms a corner of the housing upper part.

According to a preferred embodiment of the inventive idea, it is provided that the length of the sealing flap along the housing lid is less than the length of the sealing flap along the side wall of the housing upper part. Even in the case of an opened sealing flap sticking out at right angles, it is not possible for test strips unintentionally to fall out of the container since the side-wall region of the sealing flap projecting over the side wall of the housing lower part or the housing upper part arranged flush therewith forms a stop face and retains the test strips in the container.

An illustrative embodiment of the inventive idea is explained in greater detail below with reference to the drawing, in which.

Figure 2:
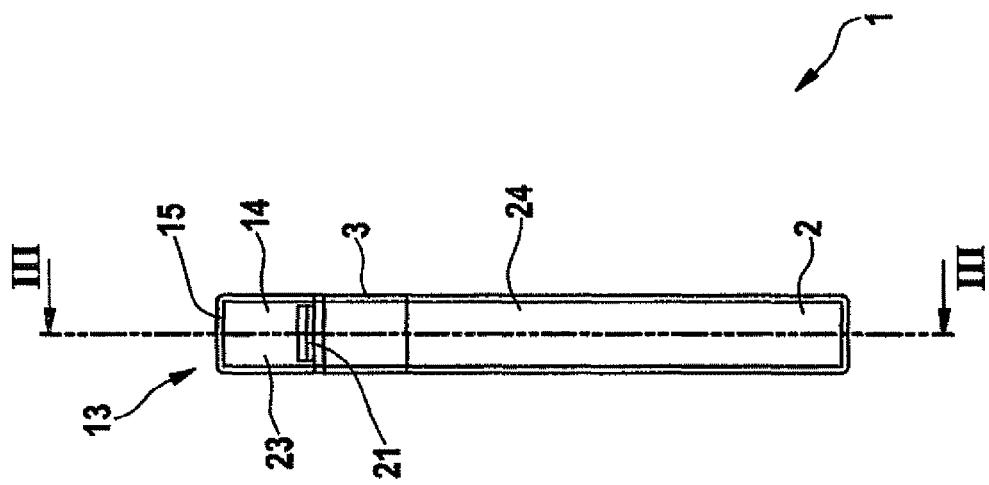
FIG. 2 shows another side view of the container depicted in FIG. 1.
Figure 1:
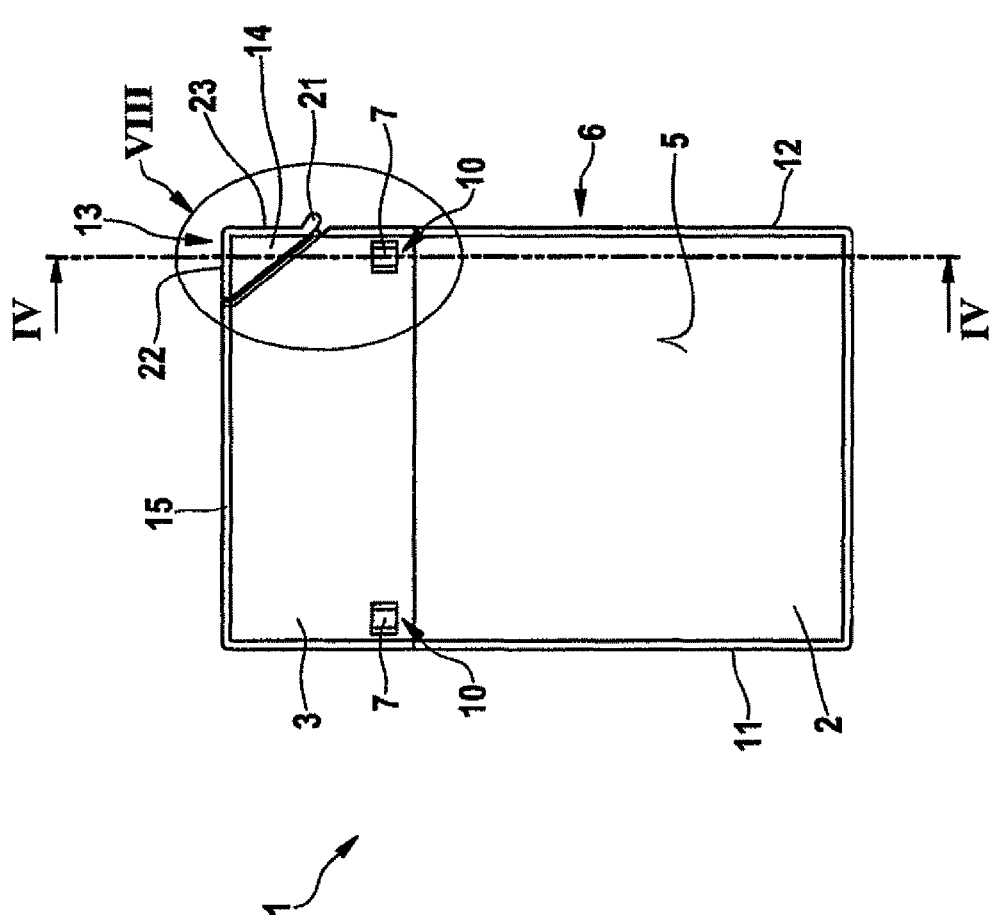
FIG. 1 shows a side view of a container for a plurality of test strips.
Figure 4:
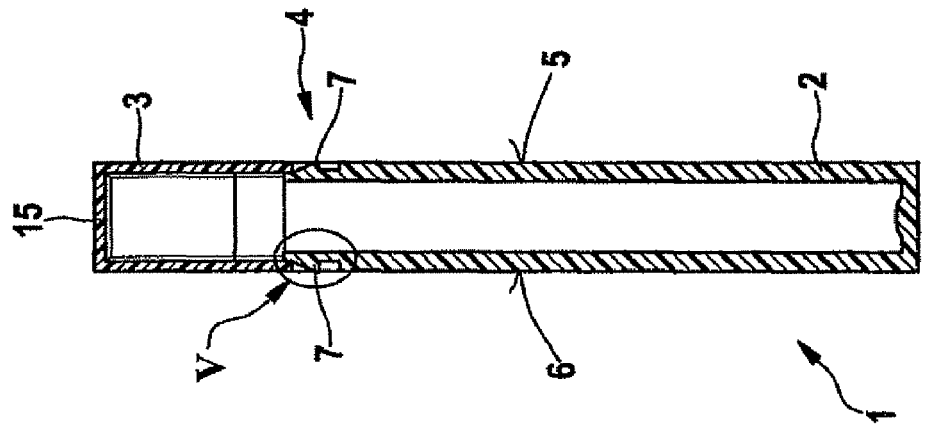
Figure 3:
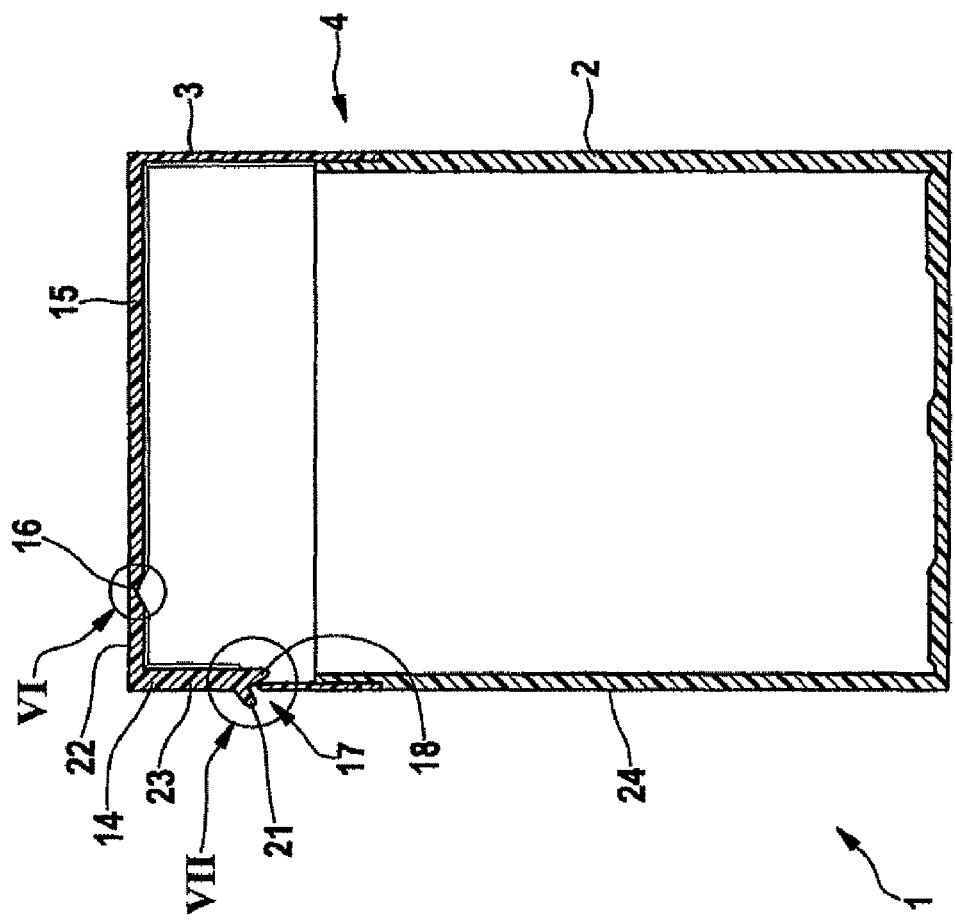
Figure 5:
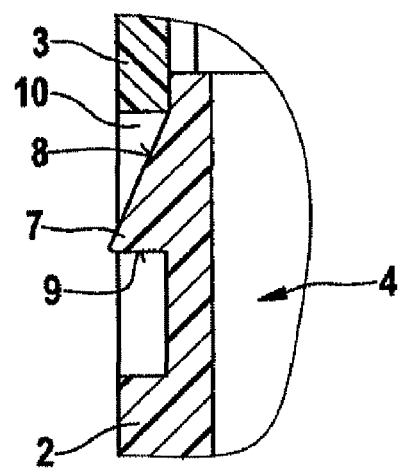
Figure 6:
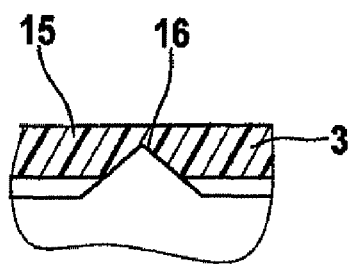
Figure 7:
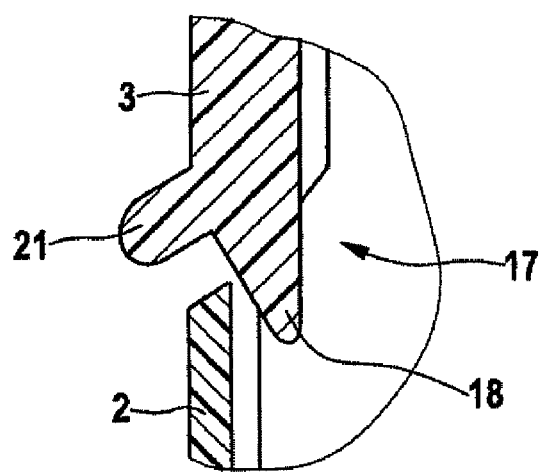
Figure 8:
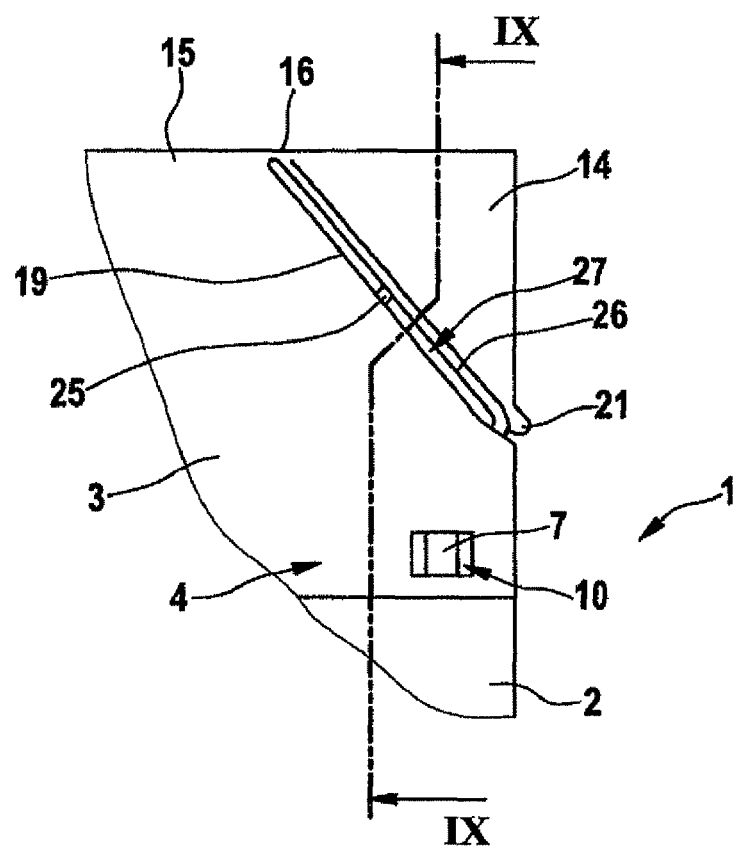
Figure 9:
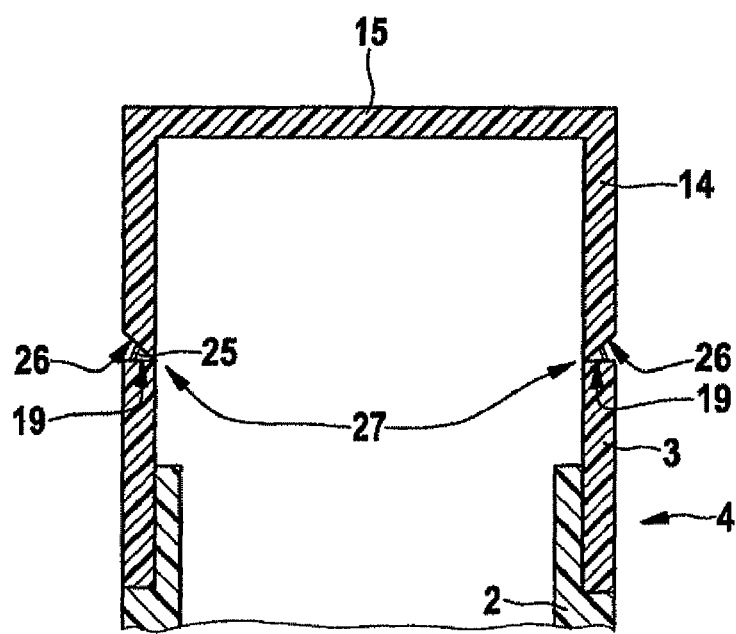
Figure 10:
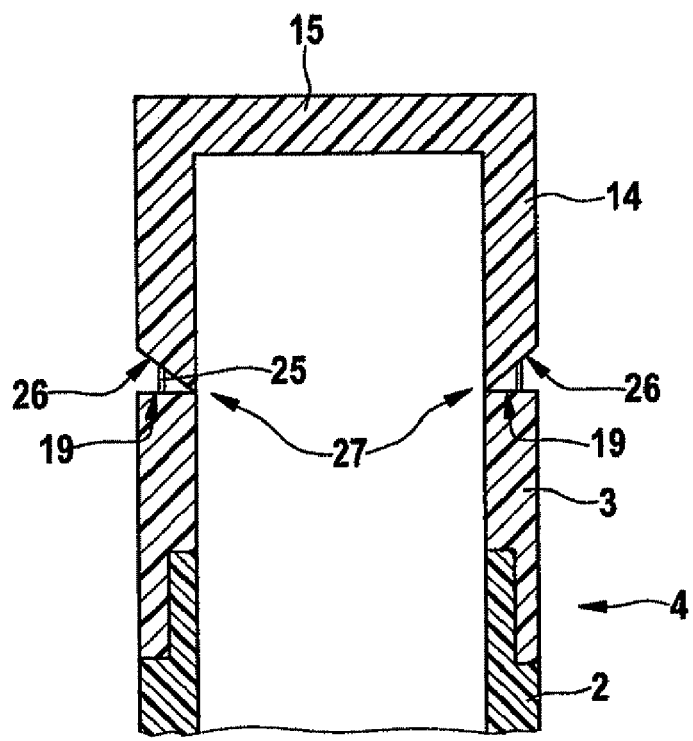
Figure 11:
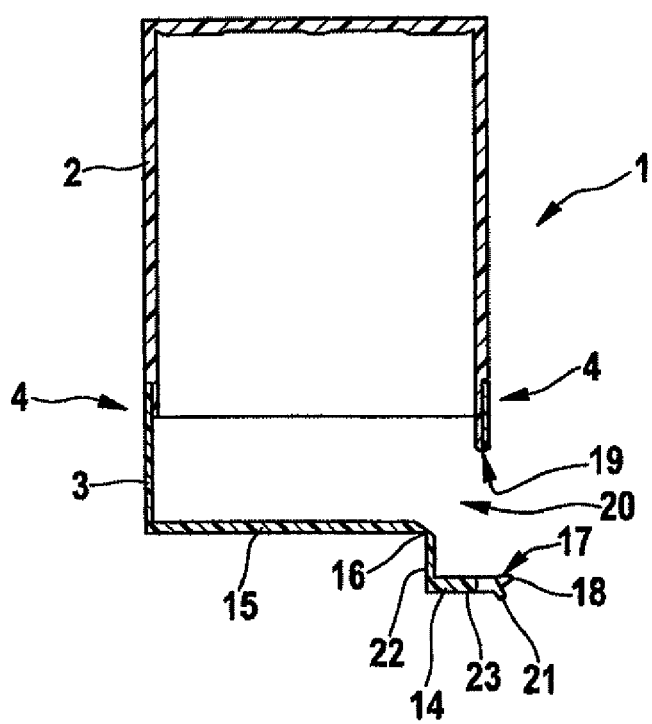

FIG. 3 shows a sectional view of the container depicted in FIGS. 1 and 2 along line in FIG. 2, FIG. 4 shows a sectional view of the container depicted in FIGS. 1 and 2 along line IV-IV in FIG. 1, FIG. 5 shows an enlarged section indicated by V in FIG. 4, FIG. 6 shows an enlarged section indicated by VI in FIG. 3, FIG. 7 shows an enlarged section indicated by VII in FIG. 3, FIG. 8 shows an enlarged section indicated by VIII in FIG. 1, FIG. 9 shows a sectional view of the section depicted in FIG. 8 along line IX-IX, and FIG. 10 shows a view, corresponding to the view in FIG. 9, of an alternative embodiment of a housing upper part of the container depicted in FIG. 1, and FIG. 11 shows a side view of the container depicted in FIG. 1 with an opened sealing flap.

The container 1 depicted in the figures for a plurality of test strips, in particular for a relatively large number of strip-shaped indicator sticks, has an essentially cuboid housing lower part 2 open on one side and a likewise essentially cuboid housing upper part 3 open on one side. The housing upper part 3 has been pushed onto the housing lower part 2 and connected thereto in a snap-fit manner to form a container 1 which is closed on all sides for test strips located therein, which are not shown in the figures.

The housing lower part 2 has a reduced wall thickness in an edge region 4 facing the housing upper part, so that the housing upper part 3 with a matched wall thickness can be pushed onto the housing lower part 2 in such a way that the outside surfaces of the housing lower part 2 and the housing upper part 3 abut one another in a flush manner.

The housing lower part 2 has outwardly projecting snap-in elements 7 arranged in the edge region 4 on each of a front side 5 and a rear side 6. The snap-in elements 7 have an inclined sliding surface 8 on a side facing the housing upper part 3 and a stop face 9 projecting perpendicular to the front side 5 or the rear side 6 on the side facing the housing lower part 2. This shape of the snap-in elements 7 has the effect that the housing upper part 3 can be pushed onto the housing lower part 2 with relatively little force until the snap-in elements 7 engage with matched recesses 10 in the housing upper part 3.

As soon as the housing upper part 3 has been pushed fully onto the housing lower part 2, the stop faces 9 of the snap-in elements 7, which are aligned perpendicular to the surface, form a positive connection in combination with the edge regions of the recesses 10, which can no longer be disconnected non-destructively, even on application of considerable force.

Since the snap-in elements 7 or the matched recesses 10 are in each case arranged in the region of side edges 11, 12 of the housing lower part 2 or housing upper part 3, the front side 5 or rear side 6 of the housing upper part cannot be deformed and lifted from the front side 5 or rear side 6 of the housing lower part so that the edge regions of the recesses 10 would be fully separated from the stop faces 9 of the snap-in elements 7 and the housing upper part 3 could be pulled off the housing lower part 2 in an unhindered manner.

As can be seen, in particular, from FIG. 5, the snap-in elements 7 in the region of the stop face 9 project by more than one wall thickness of the housing upper part in the region around the recesses 10. In this way, undesired detachment of the housing upper part 3 from the housing lower part 2 can reliably be avoided. Depending on the respective material used, in particular for the housing upper part 3, it may also be sufficient for the snap-in elements 7 to project merely by less than one wall thickness.

The housing upper part 3 has a sealing flap 14 forming a corner 13 of the housing upper part 3. The sealing flap 14 is mounted in a pivotable manner on an upper side of the housing upper part 3 in the region of a housing lid 15. For this purpose, the sealing flap 14 is made in one piece with the housing lid 15 and connected via a wall-thickness reduction 16, depicted in enlarged form in FIG. 6, which forms a film hinge. The wall-thickness reduction 16 produces a narrow region of the housing lid 15 of reduced rigidity or increased elasticity, which facilitates simple pivoting of the sealing flap 14 for opening and sealing the container 1.

On the side edge 17 opposite the wall-thickness reduction 16, the sealing flap 14 has a projecting snap-in tongue 18. The snap-in tongue 18 engages, in a closed state of the sealing flap 14, behind an edge 19 of an opening 20 in the housing upper part 3 which is covered by the sealing flap 14. By means of the snap-in tongue 18, the sealing flap 14 is retained in the closed position. The sealing flap 14 has an outward-projecting grip region 21, which simplifies grasping and opening of the sealing flap 14.

As can be seen from FIG. 1, the sealing flap 14 forms a corner 13 of the housing upper part. A first section 22 of the sealing flap 14 along the housing lid 15 is shorter than a second section 23 of the sealing flap 14 which extends along a narrow side wall 24. If the sealing flap 14 is opened so that it sticks out at right angles, the longer second section 23 extends flush with the housing lid 15 beyond the narrow side wall 24, so that test strips located in the container 1 cannot fall out, even if the container 1 is rotated and inverted.

In FIGS. 8 and 9, the container 1 is, for clarification, enlarged in the region of the sealing flap 14 and depicted in side or sectional view. The sealing flap 14 is connected to the remainder of the housing upper part 3 via two tear-off connecting strips 25. In order to open the container 1 for the first time, the tear-off connecting strips 25 must be torn off or separated before the sealing flap 14 can be pivoted from the closed position into an opened position. The connecting strips 25 then torn off indicate that the container 1 or the sealing flap 14 has already been opened once and protection of originality for the test strips located in the container 1 is no longer guaranteed.

A lower edge 26 of the sealing flap 14 narrows to a point. Between the lower edge 26 of the sealing flap 14 and the edge 19 of the opening 20 in the housing upper part 3, a separation join 27 is formed. The connecting strips 25 are moulded in one piece with the housing upper part 3 and, as narrow connecting strip 25 having a reduced wall thickness, connect the sealing flap 14 to the remainder of the housing upper part 3.

The wall thickness of the housing lower part 2 is reduced by exactly the wall thickness of the housing upper part 3 in the edge region 4 of the overlap by the housing upper part 3. The housing upper part 3 can be pushed onto the housing lower part 2 in such a way that the outside surfaces of the housing upper part 3 are subsequently aligned and arranged flush and jointlessly with the corresponding outside surfaces of the housing lower part 2. Gaps or joins and projecting shapes, which could simplify or facilitate mechanically forced separation and detachment of the housing upper part 3 from the housing lower part 2, are thus avoided.

FIG. 10 shows an alternative design of the housing upper part 3. The wall thickness of the housing upper part 3 corresponds to the wall thickness of the housing lower part 2. In the edge region 4 of the overlap, both the wall thickness of the housing upper part 3 and also the wall thickness of the housing lower part 2 are each reduced to half, so that not only the respective outside surfaces of the housing upper part 3 and of the housing lower part 2 abut one another in a flush and jointless manner, but also the respective inside surfaces are aligned and arranged flush to one another and without projecting edges.

FIG. 11 shows, for clarification, the container 1 with opened sealing flap 14 arranged upside down. The second section 23 of the sealing flap 14, which is aligned parallel to the housing lid 15 in the state of the sealing flap 14 opened at right angles, projects beyond the narrow side wall 24 and prevents test strips located in the container 1 from falling out even in the case of a container 1 arranged upside down and an opened sealing flap 14. Since one or more test strips in the region of the sealing flap 14 partly slide out and are only retained by the second section 23 of the sealing flap 14, these test strips in the region of the opening 20 are freely accessible on the sealing flap 14 and can be removed individually in a simple, rapid and reliable manner.

The housing upper part 3 and the housing lower part 2 are each preferably made in one piece from a plastic, such as, for example, polystyrene (PS) or polypropylene (PP), by injection moulding. It is advantageous here for the housing upper part 3 to be made from an elastic plastic material, such as, for example, polypropylene (PP) or polyethylene (PE). The housing lower part 2 advantageously consists of a plastic having sufficient rigidity, or strength, such as, for example, polystyrene (PS). In order to allow a user to see the contents of the container 1, the housing lower part 2 and/or the housing upper part 3 can be made from a highly transparent plastic. In the region of the snap-in elements 7, the mould used for the injection process can have movably mounted slides in order to be able to produce the undercuts depicted in the illustrative embodiment in the region of the snap-in elements 7.

The present description enables the person skilled in the art to use the invention comprehensively. Even without further comments, it is therefore assumed that a person skilled in the art will be able to utilise the above description in the broadest scope. In the case of any lack of clarity, it goes without saying that the cited publications and patent literature should be consulted. Correspondingly, these documents are regarded as part of the disclosure content of the present description.

For better understanding and in order to illustrate the invention, examples are given which are within the scope of protection of the present invention. These examples also serve to illustrate possible variants. Owing to the general validity of the inventive principle described, however, the examples are not suitable for reducing the scope of protection of the present application to these alone.

Unless expressly characterised as a feature essential to the invention, it goes without saying to the person skilled in the art that the dimensions or relative size ratios described or depicted in the illustrative embodiments are merely intended to illustrate possible variants of the inventive principle in each case, without being tied to a restriction to these dimensions or size ratios.

The invention claimed is:

1. Container for a plurality of test strips the form of strip-shaped indicator sticks, the housing having a housing lower part (2) and a housing upper part (3), which housing upper part (3) can be brought into engagement with the housing lower part (2) in a positive manner, the housing upper part (3) having an opening (20) with a sealing flap (14) mounted in a pivotable manner, the housing lower part (2) having a plurality of projecting snap-in elements (7), which can be brought into engagement with matched recesses (10) of the housing upper part (3), and the sealing flap (14) being connected along its periphery to the housing upper part (3) by at least one connecting strip (25) which can be torn off, the opening (20) which is sealed by the sealing flap (14) encompasses both a region of a housing lid (15) and a region of a side wall (24) of the housing upper part (3), the sealing flap (14) being mounted in a pivotable manner on the housing lid (15) of the housing upper part (3) and forming a corner (13) of the housing upper part (3) with the length of the sealing flap (14) along the housing lid (15) being less than the length of the sealing flap (14) along the side wall (24) of the housing upper part (3).

2. Container according to claim 1, characterized in that the snap-in elements (7) project by more than half the wall thickness of the housing upper part (3) in the region around the recesses (10), preferably by more than three quarters of the wall thickness and particularly preferably by more than one wall thickness of the housing upper part (3).

3. Container according to claim 1, characterized in that the snap-in elements (7) are arranged in the region of side edges (11, 2) of the housing lower part (2).

4. Container according to claim 1, characterized in that the wall thickness of the housing lower part (2) is reduced by at least the wall thickness of the housing upper part (3) in the region of the overlap by the housing upper part (3).

5. Container according to claim 1, characterized in that both the wall thickness of the housing lower part and also the wall thickness of the housing upper part are essentially comparable and are each reduced matched to one another in the region of the overlap.

6. Container according to claim 1, characterized in that the sealing flap (14) has at least one tear-off connecting strip (25) on each of two opposite sides.

* * * * *